(12) United States Patent
Holtsch

(10) Patent No.: US 7,370,392 B2
(45) Date of Patent: May 13, 2008

(54) LOCKING DEVICE

(75) Inventor: Peter Holtsch, Taunusstein (DE)

(73) Assignee: Holtsch Medizinprodukte GmbH, Tausstein (DE)

( * ) Notice: Subject to any disclaimer, the term of this patent is extended or adjusted under 35 U.S.C. 154(b) by 58 days.

(21) Appl. No.: 11/238,404

(22) Filed: Sep. 29, 2005

(65) Prior Publication Data

US 2006/0260103 A1  Nov. 23, 2006

(51) Int. Cl.
*A44B 11/10* (2006.01)

(52) U.S. Cl. ........................ 24/170; 24/136 R; 24/657; 24/658; 606/157; 606/151; 606/203

(58) Field of Classification Search .............. 24/134 R, 24/170, 191, 657, 658; 606/203
See application file for complete search history.

(56) References Cited

U.S. PATENT DOCUMENTS

| | | | | |
|---|---|---|---|---|
| 2,965,942 A | * | 12/1960 | Carter | 24/170 |
| 3,252,193 A | * | 5/1966 | Matthews et al. | 24/170 |
| 4,102,343 A | * | 7/1978 | Schneider | 606/203 |
| 4,640,281 A | * | 2/1987 | Sturm et al. | 606/203 |
| 4,795,384 A | * | 1/1989 | Hattori | 441/64 |
| 5,314,437 A | * | 5/1994 | Holtsch | 606/157 |
| 5,535,485 A | * | 7/1996 | Kirchner | 24/170 |
| 6,694,578 B1 | * | 2/2004 | Nicoll | 24/645 |

FOREIGN PATENT DOCUMENTS

GB   2138490 A   * 10/1984

* cited by examiner

*Primary Examiner*—Robert J. Sandy
*Assistant Examiner*—Marcus Menezes
(74) *Attorney, Agent, or Firm*—Michael J. Striker

(57) ABSTRACT

A locking device has a band provided with a locking element on its one end, a housing, a rocker turnably movable relative to the housing and having an edge which in a closed position of the device applies pressure to the band and stops the band from movement, the locking element provided on the end of the band being engageable with the housing, a first unit for turning the rocker and releasing the pressure on the band so that the band is released and can be moved but the locking element can not disengage from the housing, and a second separate unit which, upon release of the pressure on the band and application of an action to the second unit by a user, release the locking element from the housing in a next step so as to disengage the element from the housing and to open the locking device.

6 Claims, 8 Drawing Sheets

LOCKING DEVICE

BACKGROUND OF THE INVENTION

The present invention relates to locking devices, and can be used in particular for constricting devices for body parts, such as a vein constrictor.

Devices of the above mentioned general type are known in the art. One of such devices is disclosed in my U.S. Pat. No. 5,314,437. It has an elastic band to form a loop around the body part to be constricted. When the band is tightened by pulling of its free end, the force which occurs at the end connected to a housing of the device turns the clamping rocker to its clamping position in which it arrests the band in its constricting condition.

In the device disclosed in my patent when a pressure is applied to convert the device into a closed position, a cap connected with one end of the band is snapped into a housing of the device. After the use of the device, when a pressure is applied to the clamping rocker, it turns so that its clamping edge releases the band, and the band due to the restoring force can slide automatically to release the band. At the same time, a further turning movement of the clamping rocker under the action of the pressure applied in the same direction leads to opening of an arresting closure, or in other words removal of the cap from the housing.

This construction has however the disadvantage that by operating the clamping rocker exclusively, the release of the band and the opening of the closure are performed simultaneously and very fast, so that the cap with the band can "jump" from a remaining part of the device, thus causing uneasiness for a user.

SUMMARY OF THE INVENTION

Accordingly, it is an object of the present invention to provide a locking device, such as for example a constricting device for body parts, which eliminates the disadvantages of the prior art.

In keeping with these objects and with others which will become apparent hereinafter, one feature of the present invention resides, briefly stated, in a locking device, comprising a band provided with a locking element on its one end; a housing; a rocker turnably movable relative to said housing and having an edge which in a closed position of the device applies pressure to the band and stops the band from movement, said locking element provided on said end of the band being engageable with said housing; first means for turning said rocker and releasing the pressure on the band so that the band is released and can be moved but said locking element can not disengage from said housing; and second separate means which, upon release of the pressure on the band and application of an action to said second unit by a user, release said locking element from said housing in a next step so as to disengage said element from said housing and to open the locking device.

In the new device in accordance with the present invention the functions of releasing a tension of the band is separated from the function of opening of the arresting closure.

In accordance with the present invention, the device is designed so that first a key is pressed to release tension of the band, but the closure can not be open. Only thereafter by pushing of buttons provided in the device, the closure can be open. Thus, the device is designed so that there are two independent steps in the operation of the device after its use. Upon pressing of the key the cap with the band can not "jump" as before, since the device is still not completely open. Only thereafter, when the buttons are pressed by the user, the cap attached to the end of the band is released and can be withdrawn from the housing without any unexpected movements of the parts of the device.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
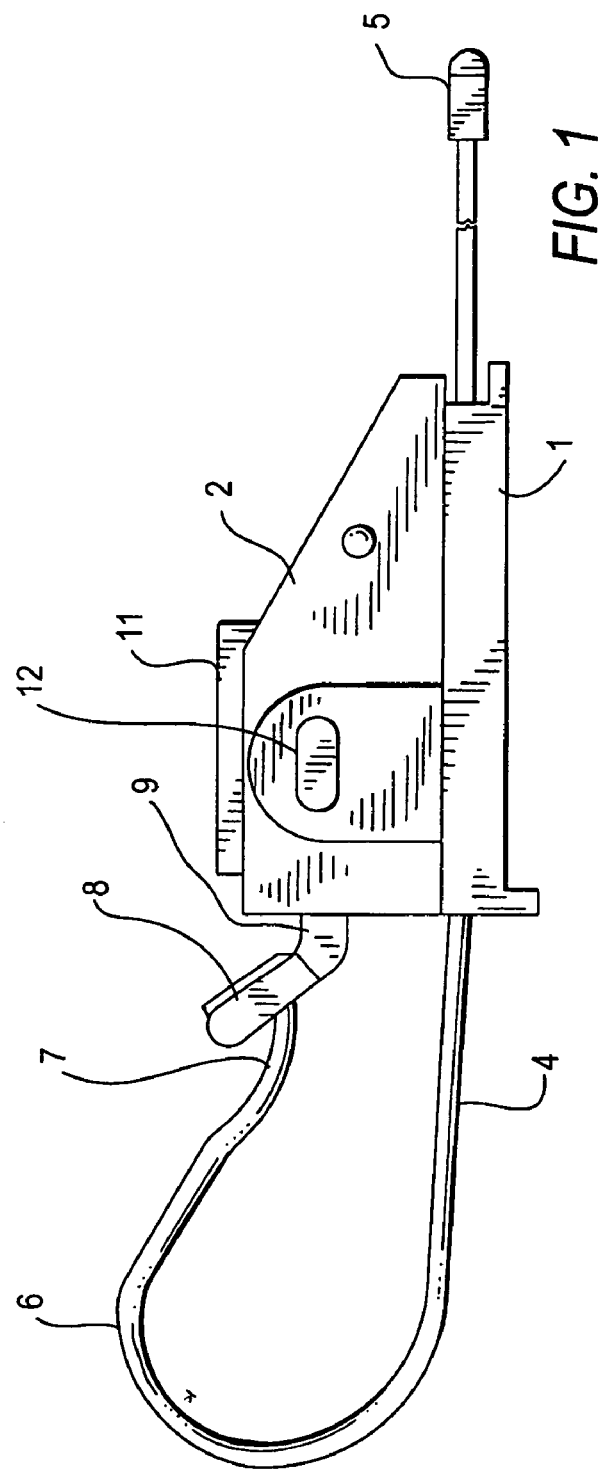
FIG. 1 is a side view of a locking device in accordance with the present invention.

A locking device in accordance with the present invention for example for constricting body parts, has a housing which is identified as a whole with reference numeral 1. A rocker 2 is mounted on the housing 1 pivotally around an axis formed for example by a pin 3 which extend through side walls of the housing 1 and the rocker 2 in assembled condition.

The locking device further has a band which is identified with reference numeral 4 and extends through a slot formed between the housing 1 and the rocker 2. The band 4 has one end 5 which a user can grasp so as to move the band 4 along the slot 2 to reduce a loop 6 formed by the band around a body part to be constricted. An opposite end 7 of the band 4 is attached to a cap 8 provided with a tongue 9 which is engageable with and disengageable from the housing 1.

Reference numeral 10 identifies a right edge of the rocker 2. A key 11 is provided on the rocker for pressing by a user and performing a first step of opening of the locking device as will be explained later on. Two buttons 12 are further provided to be pressed by a user, to perform a second step for opening of the locking device as will be explained herein below.

Reference numeral 21 identifies a component which is associated with the rocker 2 and has a wedge-shaped portion associated with a wedge-shaped opening 22 in the housing 1. Two sliders 23 and 24 are further provided. They are movable relative to one another in a transverse direction and have hooks. The slider 24 has a pin 25 while the slider 23 has an associated recess 26. The operation of the inventive locking device will be now explained with reference to FIGS. 4, 5 and 6.

A user introduces for example his arm into the loop 6 formed by the band 4 and pulls the band by its end 5 to the right in the drawing so as to reduce the loop 6 and to tighten it on the arm. The rocker 2 turns around the axis of the pin 3 and its right edge 10 applies a pressure to the band 4 and clamps it in the position in which the loop 6 restricts the arm of the user, as shown in FIG. 3.

When after the use it is necessary to finalize the procedure and to remove the locking device from a user, first the key 11 provided on the rocker 2 is pressed downwardly, and the rocker 2 is turned in a counter clockwise direction so that its end 10 no longer applies the pressure to the band 4 and the band tension is released. However, the tongue 9 of the cap 8 is still engaged with the housing 1.

Figure 2:
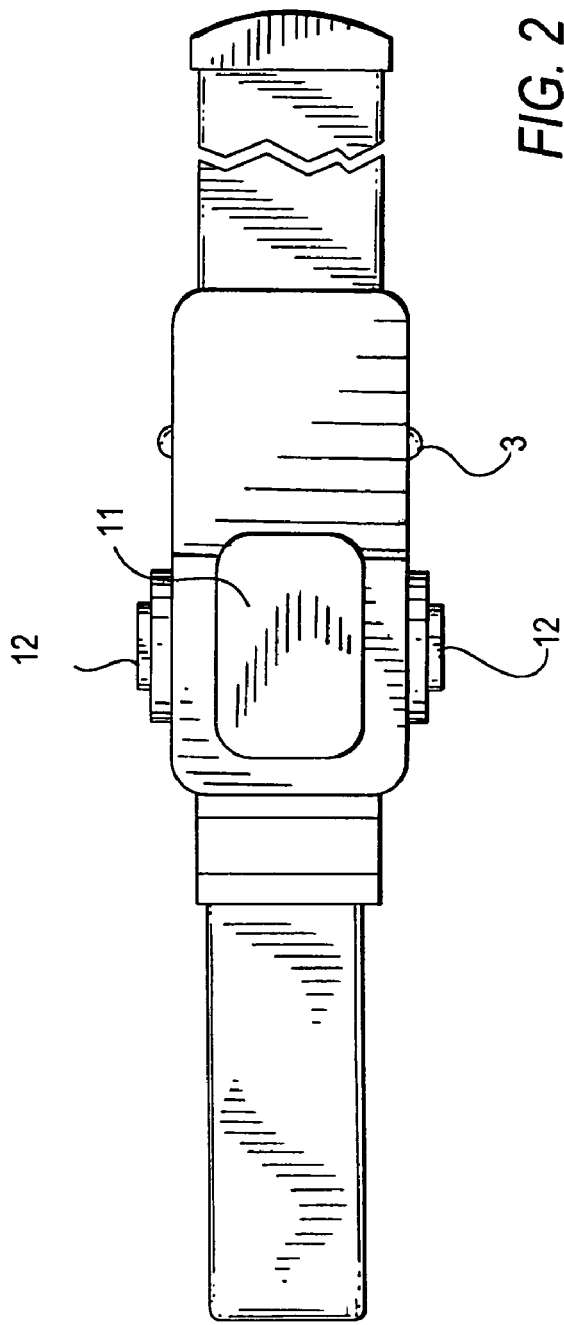
FIG. 2 is a plan view of the inventive locking device in accordance with the present invention.
Figure 4:
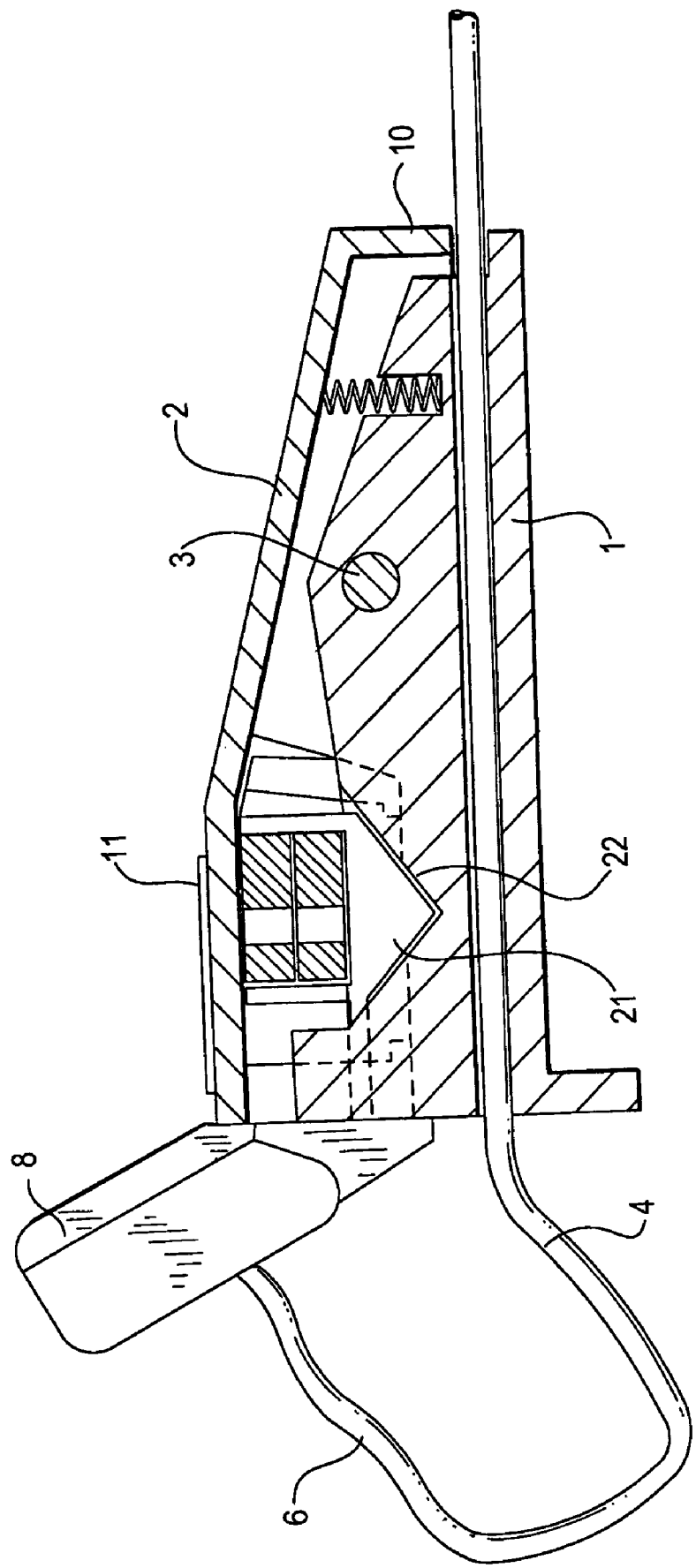
FIG. 4 is a view showing the inventive locking device in which a pressure of the band is released, but a cap attached to one end of the band still can not be disengaged from a housing of the device.
Figure 5:
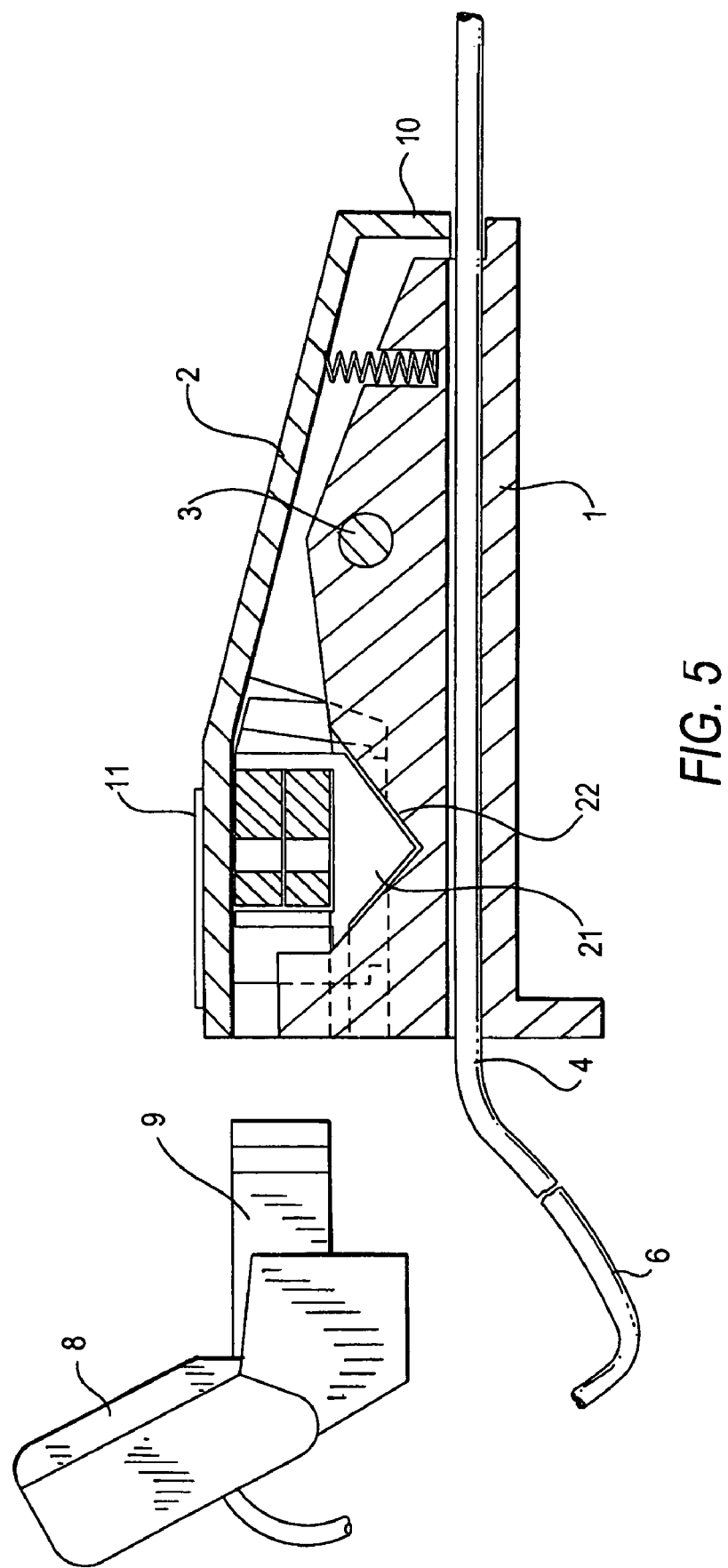
FIG. 5 is a view showing the inventive locking device in a position in which, after releasing the tension of the band, the cap on one end of the band is disengaged from the housing.

In the next step shown in FIG. 5 the user presses the buttons 12 toward one another (FIG. 2), and as a result the tongue 9 of the cap 8 is disengaged from the housing 1, so that the locking device is opened and can be removed from the arm of a user. Thus, the release of tension of the band 4 is performed in the first step shown in FIG. 4, while the disengagement of the tongue 9 of the cap 8 from the housing 1 with opening of the device is performed in the second step shown in FIG. 5. The second step is separate and independent from the previous first step and can be performed only after the first step has been completed.

Figure 3:
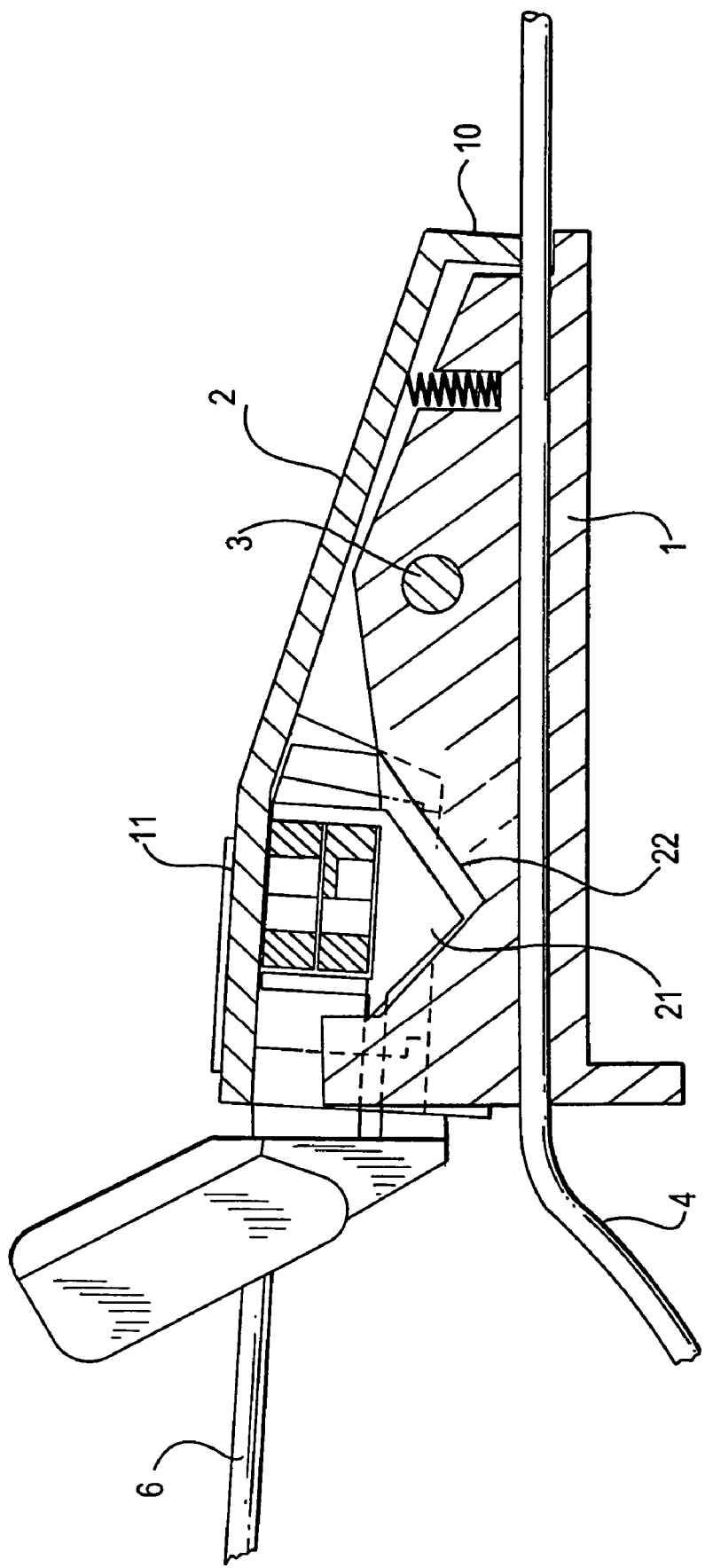
FIG. 3 is a view schematically showing a position of the inventive locking device in which a band is clamped by a rocker of the inventive locking device.

In the position shown in FIG. 3 the wedge-shaped of the component 21 associated with the rocker 2 is offset relative to the wedge-shaped opening 22 in the housing 1, while in the position shown in FIGS. 4 and 5 the wedge-shaped portion of the component 21 is completely engaged into the wedge-shaped opening 22 of the housing 1. The two sliders 23 and 24 of the locking device are movable relative to one another in a transverse direction in FIGS. 6-9 and are provided with the hooks.

Figure 6:
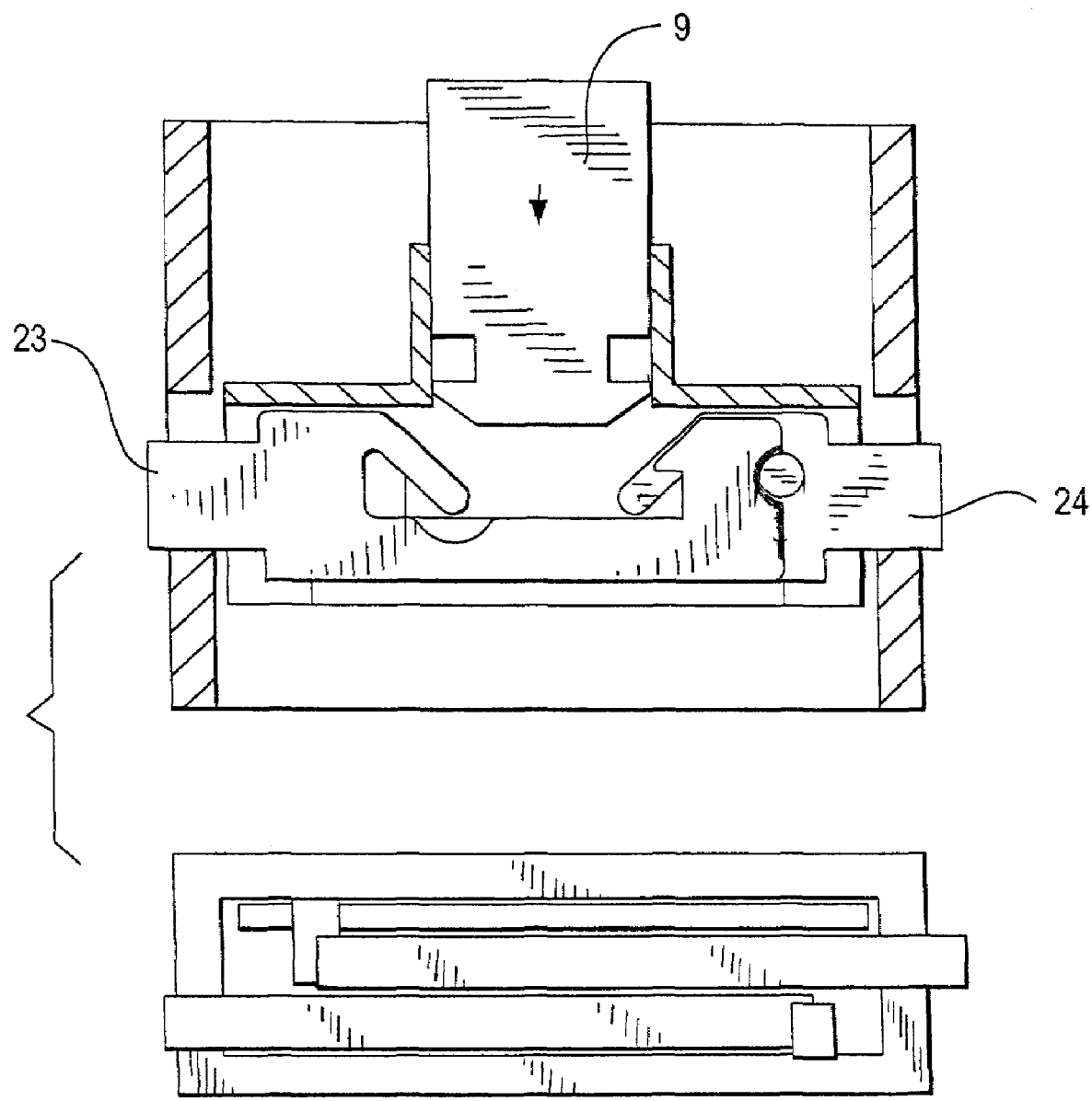
FIG. 6 is a plan view and a side view of the inventive locking device in which a tongue of the cap moves toward a closed position, and hooks of the tongue are still not engaged behind arresting cams of two sliders connected to side buttons.
Figure 7:
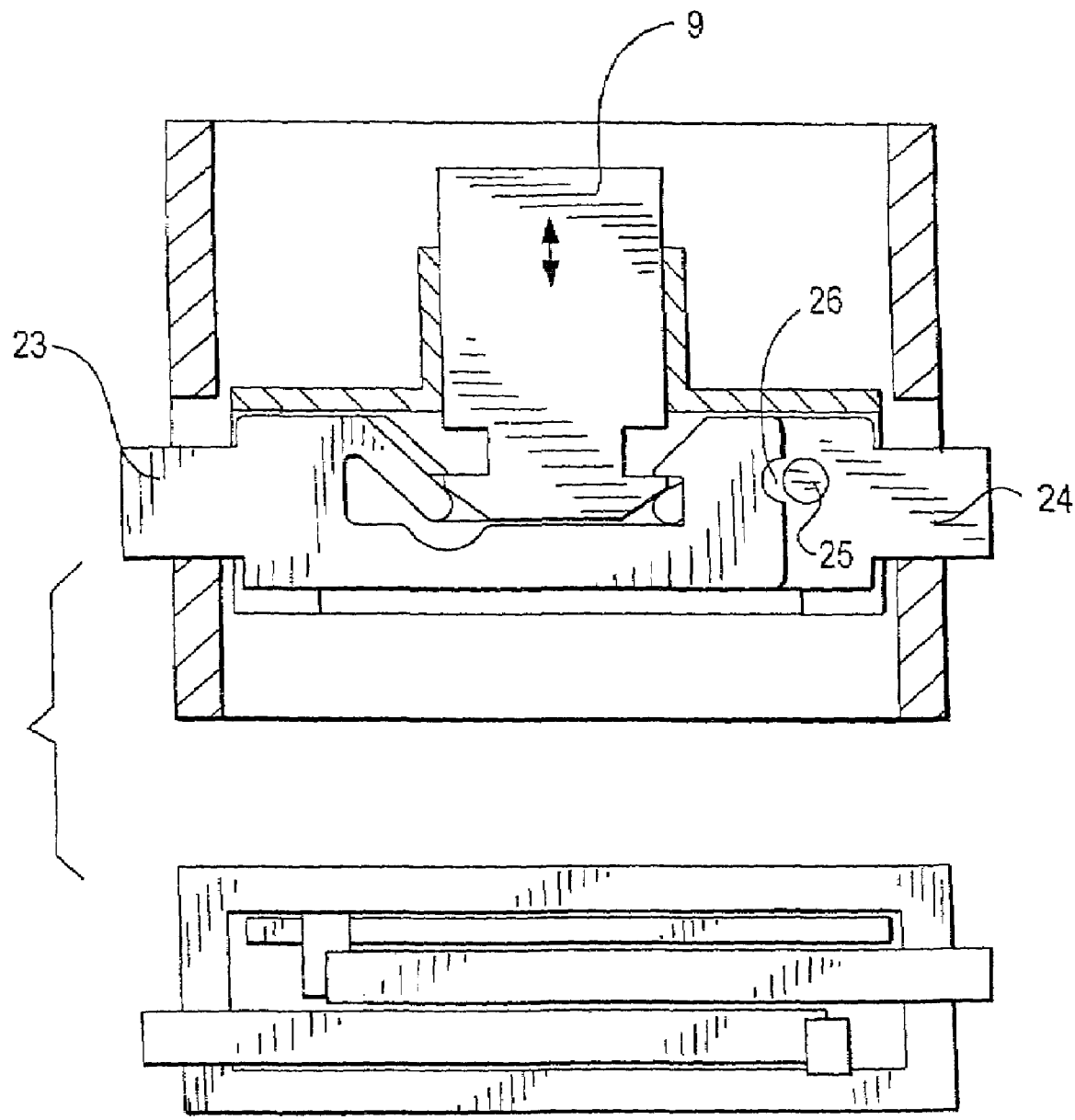
FIG. 7 is a plan view and a side view of the inventive locking device in a position in which the hooks of the tongue engage behind the arresting cams of the sliders, where there is no tension caused by a band.
Figure 8:
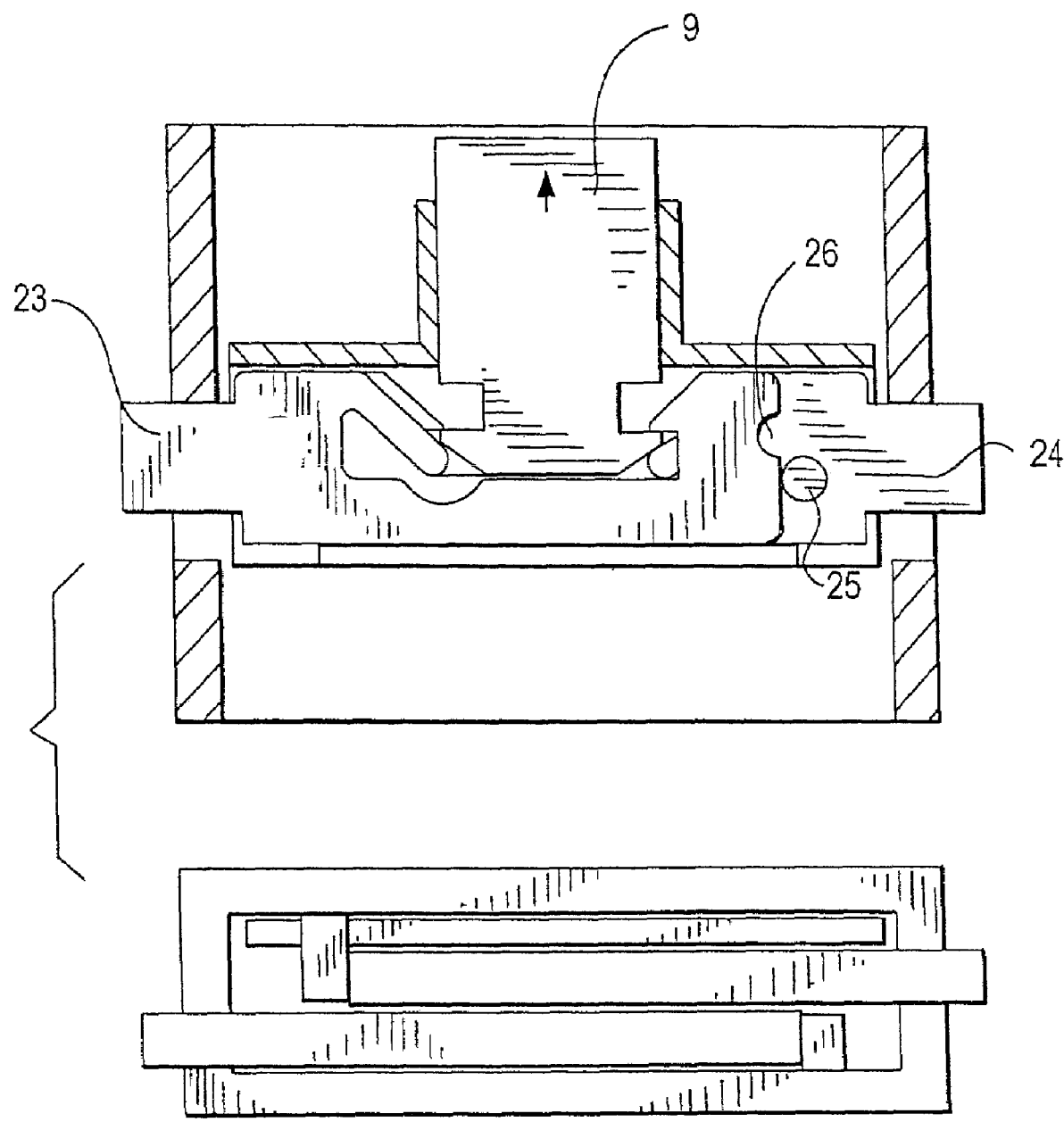
FIG. 8 is a view showing the inventive locking device in a position which substantially corresponds to the position shown in FIG. 7, but in which the band is under tension.

FIG. 6 shows a position in which the tongue 9 is moved into the housing to close the device. In the position shown in FIG. 7 the tongue 9 engages with its hooks the hooks of the sliders 23 and 24 and therefore the loop 6 of the band is closed on the arm of the user and the device is in the closed condition. The pin 25 of the slider 24 is disengaged from the recess 26 of the slider 23. The band 4 is not under tension yet. When thereafter a tension is provided in the band 4 by turning of the rocker, the pin 25 is displaced longitudinally relative to the recess 26 so that it can not engage in the recess anymore. The buttons 12 can not be pressed toward one another in this position.

Figure 9:
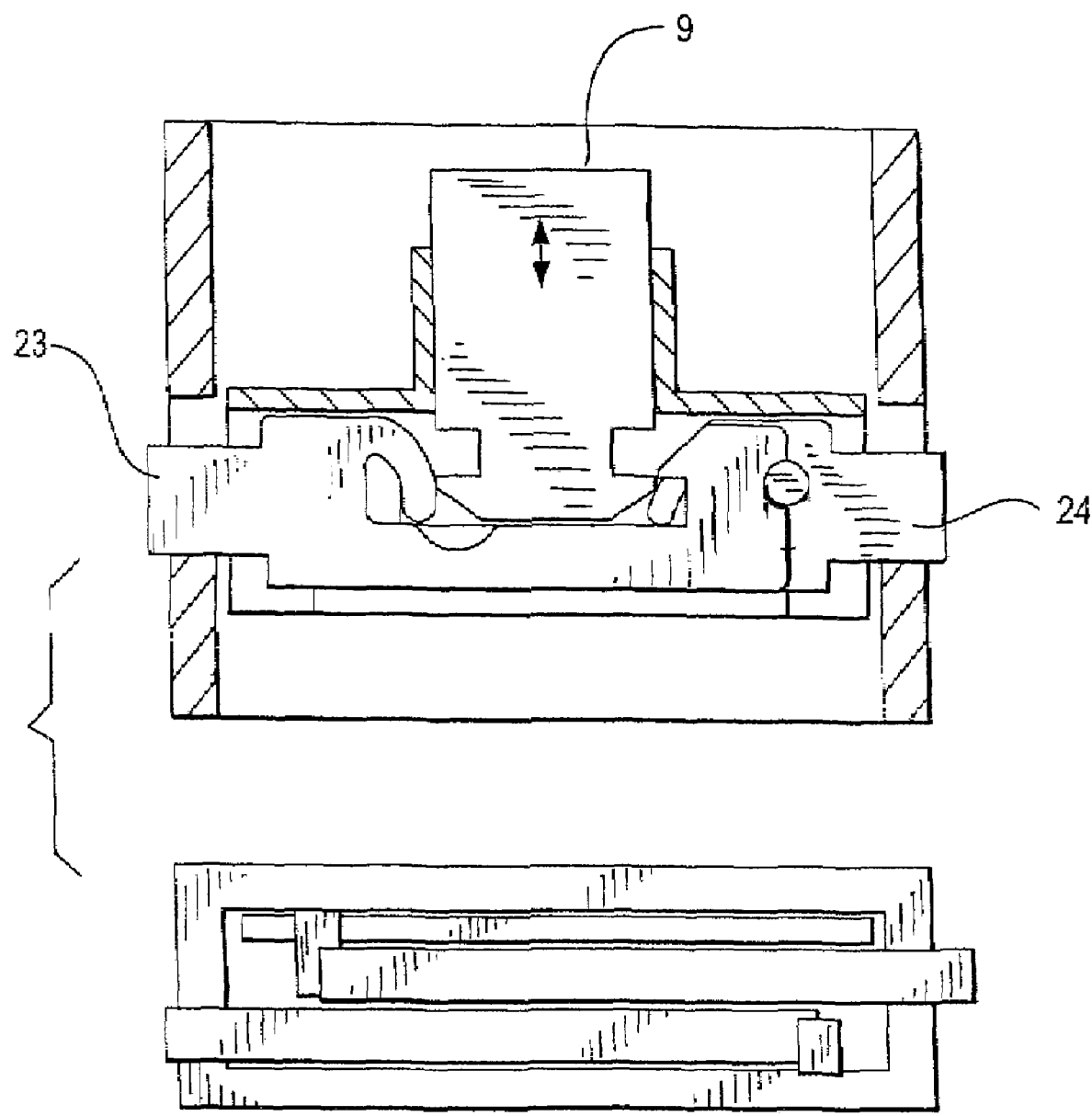
FIG. 9 is a plan view and a side view of the inventive locking device in a position in which the buttons are pushed toward one another to completely release a connection of the cap with the band from the housing.

In the position shown in FIG. 9 the key 11 is pressed down and the rocker 2 is turned clockwise so as to remove tension from the band, the slider 24 moves longitudinally upwardly in FIG. 9, and the pin 25 engages into the recess 26, so that now the buttons 12 can be pressed toward one another. As a result, the tongue 9 of the cap 8 can be disengaged from the hooks of the sliders 23 and 24, so that it can be withdrawn from the housing 1 and the device can be opened.

It will be understood that each of the elements described above, or two or more together, may also find a useful application in other types of constructions differing from the types described above.

While the invention has been illustrated and described as embodied in locking device, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

The invention claimed is:

1. A locking device, comprising a band provided with a locking element on its one end; a housing; a rocker turnably movable relative to said housing and having an edge which in a closed position of the device, after a loop formed by the band is reduced around an object to tighten the band, applies pressure to the band to stop the band from movement and to apply tension and clamp the band, said locking element provided on said end of the band being engageable with said housing and disengageable from said housing; first means, forming a part of said housing, for turning said rocker in said housing and releasing the pressure on the band so that the band is no longer tensioned and can be moved but said locking element can not disengage from said housing; and second separate means, forming a part of said housing, which, only upon release of the pressure on the band after said rocker was turned by said first means when the band is no longer tensioned and in response to an action applied to said second means, forming a part of said housing by a user, release said locking element from said housing in a next step so as to disengage said locking element from said housing and to open the locking device with the band being not tensioned, so that the band does not jump upon its release, said first and second means, forming parts of said housing being formed so that said second means can be actuated by a user only after said first means is actuated.

2. A locking device as defined in claim 1, wherein said first means include a key provided on said rocker for turning said rocker and releasing the pressure on the band without releasing said locking element.

3. A locking device as defined in claim 2, wherein said second means include push buttons which are pressable for releasing said locking element without acting on said key and turning said rocker.

4. A locking device, comprising a band provided with a locking element on its one end; a housing; a rocker turnably movable relative to said housing and having an edge which in a closed position of the device, after a loop formed by the band is reduced around an object to tighten the band, applies pressure to the band to stop the band from movement and to apply tension and clamp the band, said locking element provided on said end of the band being engageable with said housing and disengageable from said housing; first means, forming a part of said housing, for turning said rocker in said housing and releasing the pressure on the band so that the band is no longer tensioned and can be moved but said locking element can not disengage from said housing; and second separate means, forming a part of said housing, which, upon release of the pressure on the band when the band is no longer tensioned and in response to an action applied to said second means, forming a part of said housing by a user, release said locking element from said housing in a next step so as to disengage said locking element from said housing and to open the locking device with the band being arranged in said housing and not tensioned, so that the band does not jump upon its release, said first and second means, forming parts of said housing, being formed so that said second means arranged in said housing can be actuated by a user only after said first means is actuated, wherein said first means include a wedge-shaped component which when the band is under tensioned moves in a direction of the band and is introduced into a wedge-shaped opening to be offset relative to the latter, while said second means include two sliders arranged in the housing, so that when the band is tensioned a pin is disengaged from a recess of one of the sliders such that said sliders can not be moved against each other to release a tongue of the locking element connected with the band under tension, while when said first means release the tension of the band by completely introducing the wedge-shaped component into the wedge-shaped opening and the band is no longer tensioned, the pin can move into the recess of the one slider, and said sliders are moved in said housing against each other to release the tongue that is connected with the band and the tongue which is no longer under tension opens by disengaging from the housing without jumping back and without jumping of the band.

5. A locking device, comprising a band provided with a locking element on its one end; a housing; a rocker turnably movable relative to said housing and having an edge which in a closed position of the device, after a loop formed by the band is reduced around an object to tighten the band, applies pressure to the band to stop the band from movement and to apply tension and clamp the band, said locking element provided on said end of the band being engageable with said housing and disengageable from said housing; first means, for turning said rocker in said housing and releasing the pressure on the band so that the band is no longer tensioned and can be moved but said locking element can not disengage from said housing; and second separate means, which, only upon release of the pressure on the band after said rocker was turned by said first means when the band is no longer tensioned and in response to an action applied to said second means, by a user, release said locking element from said housing in a next step so as to disengage said locking element from said housing and to open the locking device with the band being not tensioned, so that the band does not jump upon its release, said first and second means, forming parts of said housing being formed so that said second means can be actuated by a user only after said first means is actuated.

6. A locking device as defined in claim 5, wherein said first means provide engagement of said second means so as not to allow said second means to be actuated before said first means is actuated, and after said first means is actuated said first means cause disengagement of said second means so that said second means can be actuated.

* * * * *